United States Patent
Aihara et al.

(10) Patent No.: US 12,079,990 B2
(45) Date of Patent: Sep. 3, 2024

(54) LEG MUSCLE STRENGTH ESTIMATION SYSTEM AND LEG MUSCLE STRENGTH ESTIMATION METHOD

(71) Applicant: Panasonic Intellectual Property Management Co., Ltd., Osaka (JP)

(72) Inventors: Takahiro Aihara, Osaka (JP); Taichi Hamatsuka, Osaka (JP); Yoshihiro Matsumura, Osaka (JP); Takashi Uchida, Hyogo (JP); Kengo Wada, Osaka (JP); Takahiro Hiyama, Tokyo (JP); Akira Matsubara, Osaka (JP); Manabu Yumine, Osaka (JP); Yoshikuni Sato, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 17/601,655

(22) PCT Filed: Feb. 7, 2020

(86) PCT No.: PCT/JP2020/004704
§ 371 (c)(1),
(2) Date: Oct. 5, 2021

(87) PCT Pub. No.: WO2020/208922
PCT Pub. Date: Oct. 15, 2020

(65) Prior Publication Data
US 2022/0198658 A1  Jun. 23, 2022

(30) Foreign Application Priority Data
Apr. 9, 2019 (JP) ................. 2019-074422

(51) Int. Cl.
G06T 7/00 (2017.01)
G06V 40/20 (2022.01)

(52) U.S. Cl.
CPC ............ *G06T 7/0012* (2013.01); *G06V 40/25* (2022.01); *G06T 2207/10016* (2013.01); *G06T 2207/20081* (2013.01); *G06T 2207/30004* (2013.01)

(58) Field of Classification Search
CPC . G06T 2207/10016; G06T 2207/20081; G06T 2207/30196; G06T 2207/30004;
(Continued)

(56) References Cited

U.S. PATENT DOCUMENTS

2007/0073514 A1\* 3/2007 Nogimori ............ G01C 22/006
702/160
2010/0035728 A1\* 2/2010 Shinomiya ........... A61B 5/1038
482/8

(Continued)

FOREIGN PATENT DOCUMENTS

JP 2005-074107 A 3/2005

OTHER PUBLICATIONS

International Search Report and Written Opinion issued in International Application No. PCT/JP2020/004704, mailed Apr. 21, 2020; with partial English translation.

(Continued)

*Primary Examiner* — Margaret G Mastrodonato
(74) *Attorney, Agent, or Firm* — Rimon P.C.

(57) ABSTRACT

A leg muscle strength estimation system includes: an obtainer that obtains an image including a user that is walking as a subject of the image; and an estimator that estimates a leg muscle strength of the user based on the obtained image.

10 Claims, 8 Drawing Sheets

(58) Field of Classification Search
CPC ......... G06T 7/0012; G06V 40/25; A61B 5/11; A61B 5/1117; A61B 5/112; A61B 5/224; A61B 5/4585
See application file for complete search history.

(56) References Cited

U.S. PATENT DOCUMENTS

2017/0316578 A1* 11/2017 Fua .................. G06T 7/246
2018/0020954 A1* 1/2018 Lillie ................ A61B 5/4585
600/476

OTHER PUBLICATIONS

Kohji Wakayoshi et. al., "Improvement of walking performance in leg training program for longterm according in elderly people with low physical fitness", Bulletin of Biwako Seikei Sport College, pp. 133-147, Mar. 15, 2009 with partial English translation.

* cited by examiner

LEG MUSCLE STRENGTH ESTIMATION SYSTEM AND LEG MUSCLE STRENGTH ESTIMATION METHOD

CROSS-REFERENCE OF RELATED APPLICATIONS

This application is the U.S. National Phase under 35 U.S.C. § 371 of International Patent Application No. PCT/JP2020/004704, filed on Feb. 7, 2020, which in turn claims the benefit of Japanese Application No. 2019-074422, filed on Apr. 9, 2019, the entire disclosures of which Applications are incorporated by reference herein.

TECHNICAL FIELD

The present invention relates to a leg muscle strength estimation system and a leg muscle strength estimation method.

BACKGROUND ART

In recent years, the number of people interested in preventing illness and maintaining health is increasing. As one example of a technique aimed at maintaining a user's health, Patent Literature (PTL) 1 discloses a health management system that improves the state of wellbeing of the user so as to attain a goal without relying on the user's willingness.

CITATION LIST

Patent Literature

[PTL 1] Japanese Unexamined Patent Application Publication No. 2005-74107

SUMMARY OF INVENTION

Technical Problem

A wearable device that is worn on the user's body and is designed to maintain a user's health is known. However, some people may find it annoying to have to wear the wearable device at all times. Accordingly, there is demand for a means that can readily obtain the user's state of health. The present invention provides a leg muscle strength estimation system and a leg muscle strength estimation method that can estimate the leg muscle strength of a user without contacting the user.

Solution to Problem

A leg muscle strength estimation system according to one aspect of the present invention includes: an obtainer that obtains an image including a user that is walking as a subject of the image; and an estimator that estimates a leg muscle strength of the user based on the image obtained.

A leg muscle strength estimation method according to one aspect of the present invention includes: obtaining an image including a user that is walking as a subject of the image; and estimating a leg muscle strength of the user based on the image obtained.

A non-transitory computer-readable recording medium according to one aspect of the present invention has recorded thereon a program for causing a computer to execute the leg muscle strength estimation method.

Advantageous Effects of Invention

The leg muscle strength estimation system and the leg muscle strength estimation method according to the present invention can estimate the leg muscle strength of a user without contacting the user.

DESCRIPTION OF EMBODIMENTS

Hereinafter an embodiment will be described with reference to the figures. The following embodiment describes a general or specific example. The numerical values, shapes, materials, elements, the arrangement and connection of the elements, steps, order of the steps, etc., shown in the following embodiment are mere examples, and therefore do not limit the scope of the present invention. Therefore, among elements in the following exemplary embodiment, those not recited in any one of the independent claims are described as optional elements.

Note that the figures are schematic drawings, and are not necessarily exact depictions. Moreover, in the figures, elements that are essentially the same share like reference signs. Accordingly, repeated description may be omitted or simplified.

Embodiment

Configuration

Figure 1:
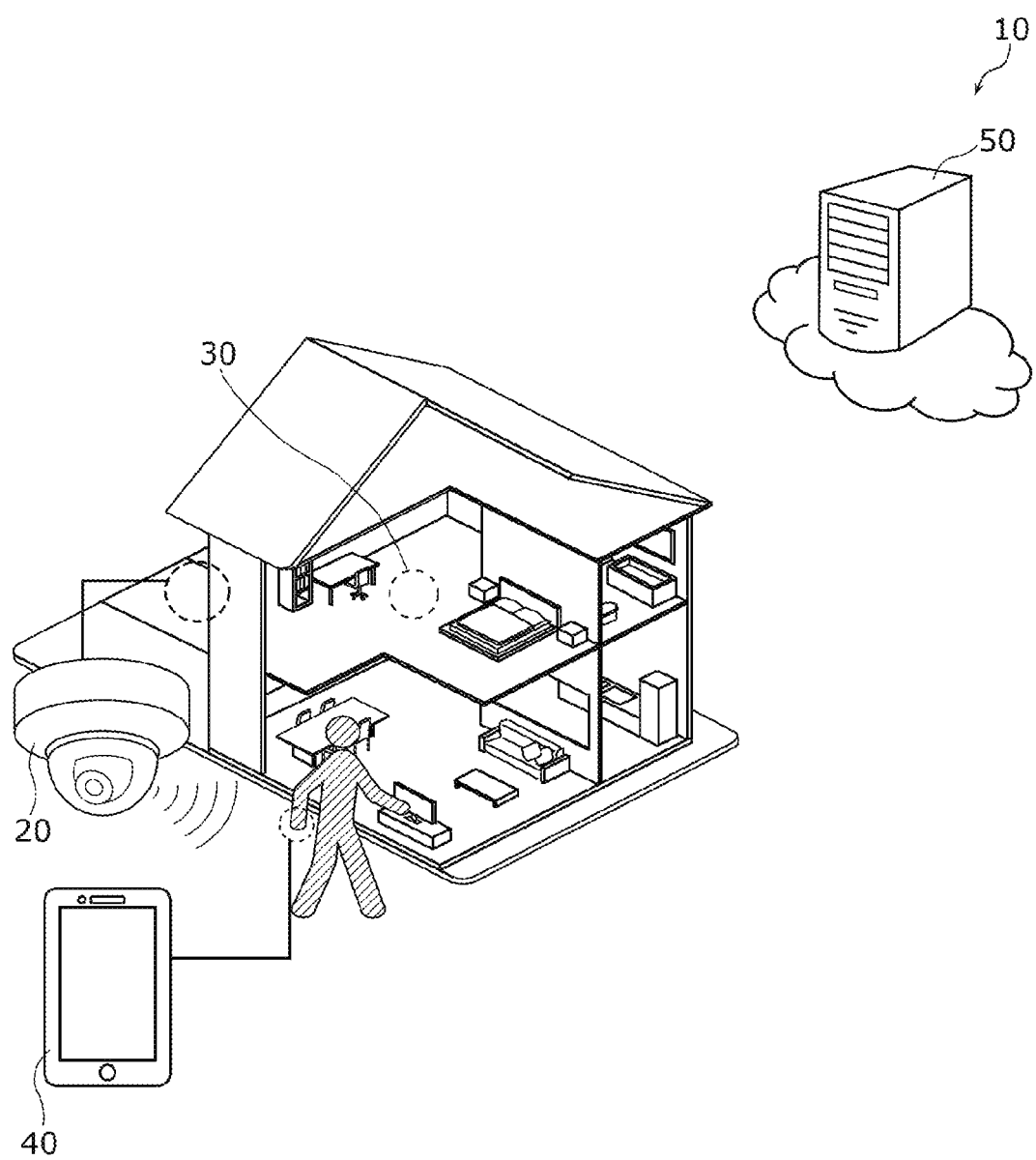
FIG. 1 illustrates an outline of a leg muscle strength estimation system according to an embodiment.
Figure 2:
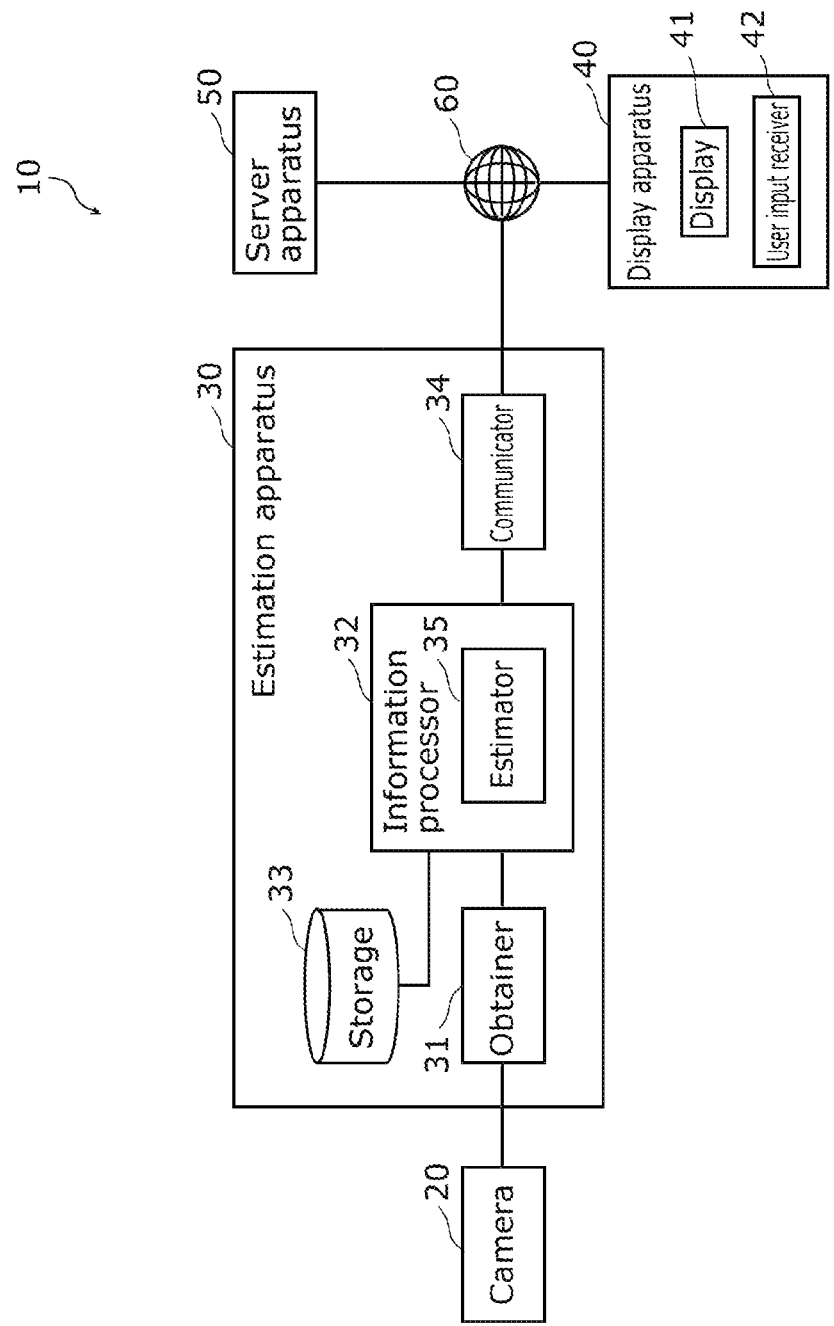
FIG. 2 is a block diagram illustrating the functional configuration of the leg muscle strength estimation system according to the embodiment.

First, the configuration of a leg muscle strength estimation system according to an embodiment will be described. FIG. 1 illustrates an outline of the leg muscle strength estimation system according to the embodiment. FIG. 2 is a block diagram illustrating the functional configuration of the leg muscle strength estimation system according to the embodiment. As illustrated in FIG. 1 and FIG. 2, leg muscle strength estimation system 10 includes camera 20, estimation apparatus 30, display apparatus 40, and server apparatus 50.

Leg muscle strength estimation system 10 is a system that obtains an image captured by camera 20 of a user while the user is walking, and estimates the leg muscle strength of the user based on the obtained image. The leg muscle strength estimation method will be described later.

Camera 20 is, for example, disposed on the exterior wall of the home of the user, and captures an image (a video comprising a plurality of images) including the walking user as the subject of the image. Camera 20 may be a camera including a complementary metal oxide semiconductor (CMOS) image sensor, and may be a camera including a charge coupled device (CCD) image sensor.

A surveillance camera or a security camera or the like that continuously captures images of the surrounding area of the home is used as camera 20. A camera for capturing images of visitors that is included in a door intercom or the like may be used as camera 20. With this, images of the user while the user is walking can be captured when the user leaves and returns home as usual and accumulated in the storage of estimation apparatus 30, without requiring any special action by the user. In other words, leg muscle strength estimation system 10 can estimate the leg muscle strength of the user without the user noticing.

Estimation apparatus 30 obtains an image captured by camera 20 and estimates the leg muscle strength of the user. Estimation apparatus 30 is, for example, a home controller that is disposed inside the user's home and is for controlling devices disposed in the home, but estimation apparatus 30 may be a personal computer or the like. Estimation apparatus 30 may be disposed inside the home at which camera 20 is disposed, and may be disposed outside the home. Estimation apparatus 30 includes, specifically, obtainer 31, information processor 32, storage 33, and communicator 34.

Obtainer 31 obtains an image (more specifically, image data) captured by camera 20. Obtainer 31 is, specifically, a communication module (communication circuit) that communicates with the camera. Obtainer 31 may communicate over wire or wirelessly. So long as obtainer 31 is capable of communicating with camera 20, the communication standard used by obtainer 31 is not particularly limited.

Information processor 32 performs information processing for estimating the leg muscle strength of the user and performs storing of the image data into storage 33. Information processor 32 includes estimator 35. Specifically, information processor 32 is implemented as a processor, a microcomputer, or dedicated circuitry. Information processor 32 may be implemented as a combination of two or more of a processor, a microcomputer, or dedicated circuitry.

Storage 33 is a storage apparatus that accumulates the image data obtained by obtainer 31. A computer program or the like for execution by information processor 32 is also stored in storage 33. Specifically, storage 33 is implemented as semiconductor memory or a hard disk drive (HDD) or the like.

Communicator 34 is a communication module (communication circuit) for estimation apparatus 30 to communicate with display apparatus 40 or server apparatus 50 via wide-area communication network 60 such as the internet. Communicator 34 may communicate wirelessly or over wire. The communication standard used for the communication is not particularly limited.

Display apparatus 40 is an information terminal including, for example, display 41 and user input receiver 42. Display 41 is, for example, a liquid crystal panel or an organic EL panel or the like, and user input receiver 42 is, for example, a touch panel or the like that receives an input made by the user. Display apparatus 40 is a portable information terminal such as a smartphone or tablet terminal or the like, but may be a stationary information terminal such as a personal computer. Display apparatus 40 is capable of communicating with estimation apparatus 30 or server apparatus 50 via wide-area communication network 60. Display apparatus 40 may communicate directly with estimation apparatus 30 without the use of wide-area communication network 60.

Server apparatus 50 is a server apparatus (cloud server) for notifying display apparatus 40 of the estimation result of the leg muscle strength by estimation apparatus 30. Server apparatus 50 is capable of communicating with estimation apparatus 30 or display apparatus 40 via wide-area communication network 60.

OPERATION EXAMPLE 1

Figure 3:
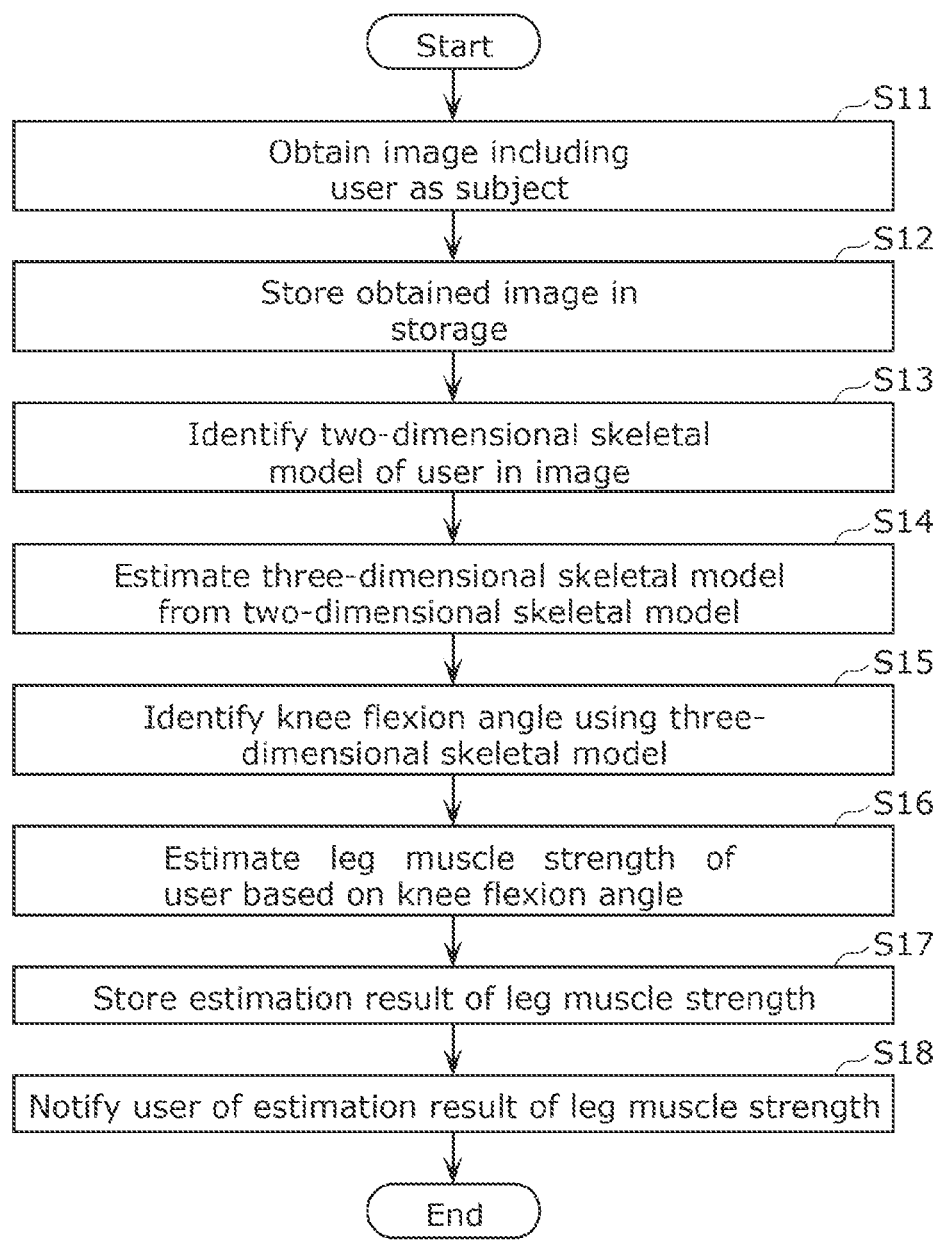
FIG. 3 is a flowchart of operation example 1 of the leg muscle strength estimation system according to the embodiment.

Next, operation example 1 of leg muscle strength estimation system 10 will be given. FIG. 3 is a flowchart of operation example 1 of leg muscle strength estimation system 10.

First, obtainer 31 of estimation apparatus 30 obtains an image including the walking user as the subject of the image from camera 20 (S11), and information processor 32 stores the obtained image in storage 33 (S12).

Figure 4:
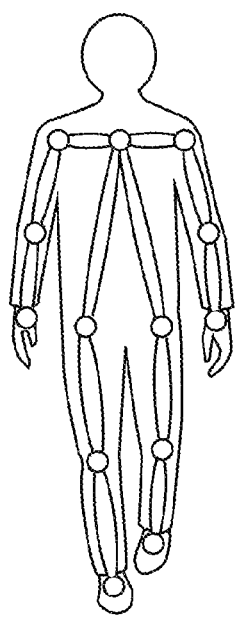
FIG. 4 conceptually illustrates the identification of a two-dimensional skeletal model of a user.

Next, estimator 35 identifies a two-dimensional skeletal model of the user captured in the image stored in storage 33 (S13). FIG. 4 conceptually illustrates the identification of the two-dimensional skeletal model of the user. As illustrated in FIG. 4, the two-dimensional skeletal model is a model that connects positions of joints (indicated by spheres) of the user captured in the image with links (lines). A known algorithm for identifying posture and the skeletal frame is used in the identification of the two-dimensional skeletal model.

Figure 5:
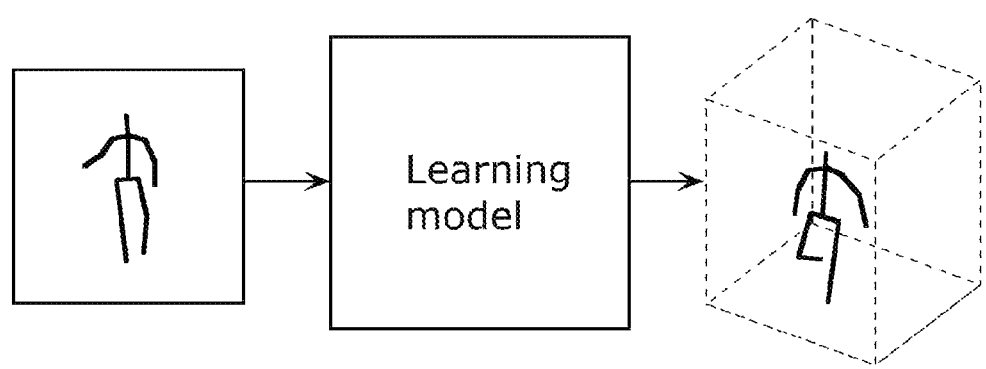
FIG. 5 conceptually illustrates the estimation of a three-dimensional skeletal model.

Next, estimator 35 estimates a three-dimensional skeletal model from the identified two-dimensional skeletal model (S14). Estimator 35 estimates the three-dimensional skeletal model using, for example, a machine learning model. FIG. 5 conceptually illustrates the estimation of the three-dimensional skeletal model. This machine learning model is a discriminator built in advance through machine learning that uses, as training data, a two-dimensional skeletal model appended with three-dimensional coordinate data for each joint as the appended answer. Such a machine learning model can output three-dimensional coordinate data (i.e., a three-dimensional skeletal model) when given an input of a two-dimensional skeletal model.

Figure 6:
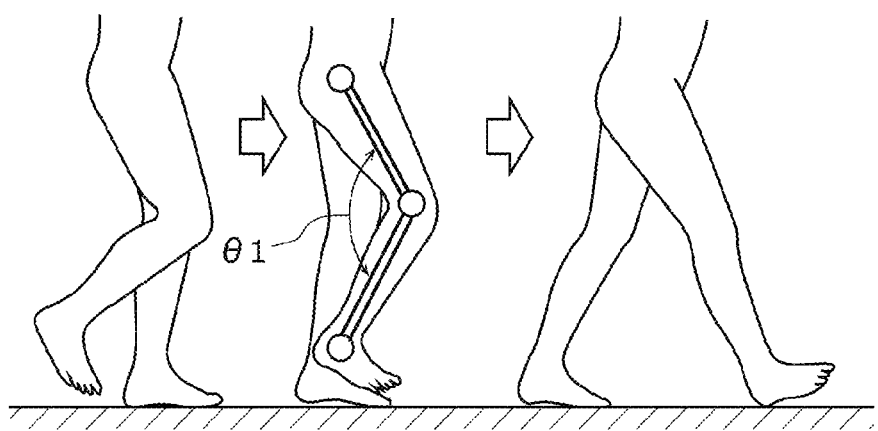
FIG. 6 is a first figure that illustrates a knee flexion angle example.
Figure 7:
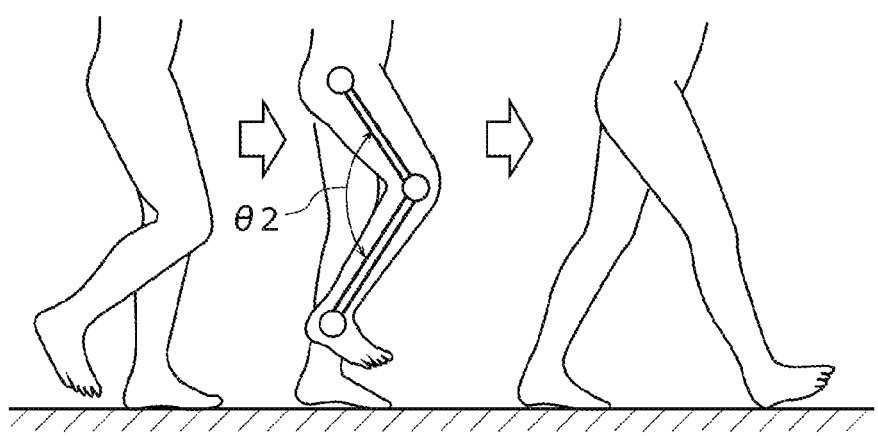
FIG. 7 is a second figure that illustrates a knee flexion angle example.

Next, estimator 35 identifies a knee flexion angle of the user while the user is walking, using the three-dimensional skeletal model (S15). Specifically, estimator 35 identifies the knee flexion angle when the knee of the leg being put forward while the user is walking is at its maximum height from the surface of the ground (i.e., the walking surface). FIG. 6 and FIG. 7 illustrate knee flexion angle examples. As described above, since the three-dimensional skeletal model is three-dimensional coordinate data for each joint, the knee flexion angle described above can be calculated.

Next, estimator 35 estimates the leg muscle strength of the user based on the identified knee flexion angle (S16). According to the inventors' knowledge, it can be concluded that the smaller the knee flexion angle of the leg being put forward while the user is walking is (stated differently, the more the knee is bent), the greater the leg muscle strength of the user is. In the examples illustrated in FIG. 6 and FIG. 7, since $\theta 1$ (FIG. 6)$>\theta 2$ (FIG. 7), it can be concluded that the leg muscle strength of the user illustrated in FIG. 7 is greater than the leg muscle strength of the user illustrated in FIG. 6. Therefore, the smaller the knee flexion angle of the user while the user is walking is, the greater estimator 35 estimates the leg muscle strength of the user to be.

Estimator 35 stores the estimation result of the leg muscle strength in storage 33 (S17). For example, estimator 35 converts the knee flexion angle into a muscle strength value and stores this value in storage 33 by using reference data that is stored in advance in storage 33 and indicates associations between knee flexion angles and muscle strength values.

Figure 8:
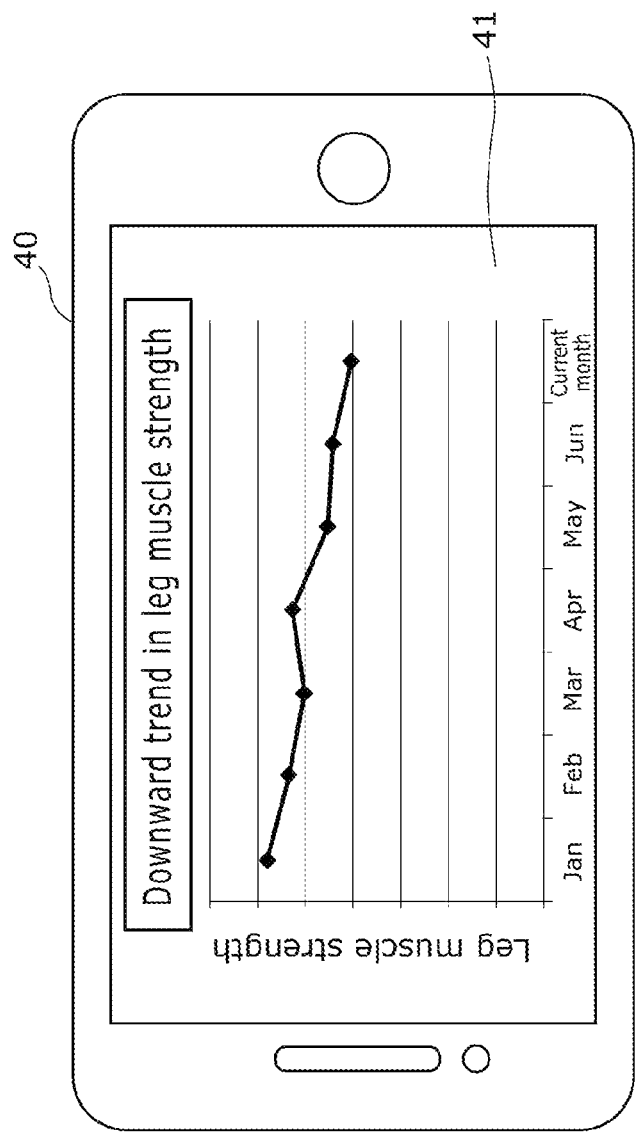
FIG. 8 illustrates one example of a notification screen for notifying the user of a decrease in leg muscle strength.

Estimator 35 then notifies the user of the estimation result of the leg muscle strength when necessary (S18). For example, estimator 35 estimates the leg muscle strength and stores the estimation result at fixed intervals, and when, for example, the data indicates a downward (or upward) trend in leg muscle strength, causes communicator 34 to transmit the notification information. The notification information is received by display apparatus 40 via server apparatus 50, and as a result, a notification screen for the leg muscle strength is displayed on display 41. FIG. 8 illustrates one example of the notification screen for notifying the user of a decrease in leg muscle strength.

Note that it is not necessary for the notification of the estimation result of the leg muscle strength to be performed from the estimation apparatus 30 side. For example, the transmission of the notification information to display apparatus 40 may be triggered by user input receiver 42 receiving a predetermined input made by the user. In other words, the notification information may be transmitted to display apparatus 40 in response to a request by the user.

As described above, in operation example 1, estimator 35 estimates the leg muscle strength of the user based on the knee flexion angle of the user while the user is walking, which is identified using an image obtained by obtainer 31. This makes it possible to easily obtain leg muscle strength data as a result of the user simply walking as usual within the image capturing range of camera 20.

OPERATION EXAMPLE 2

Figure 9:
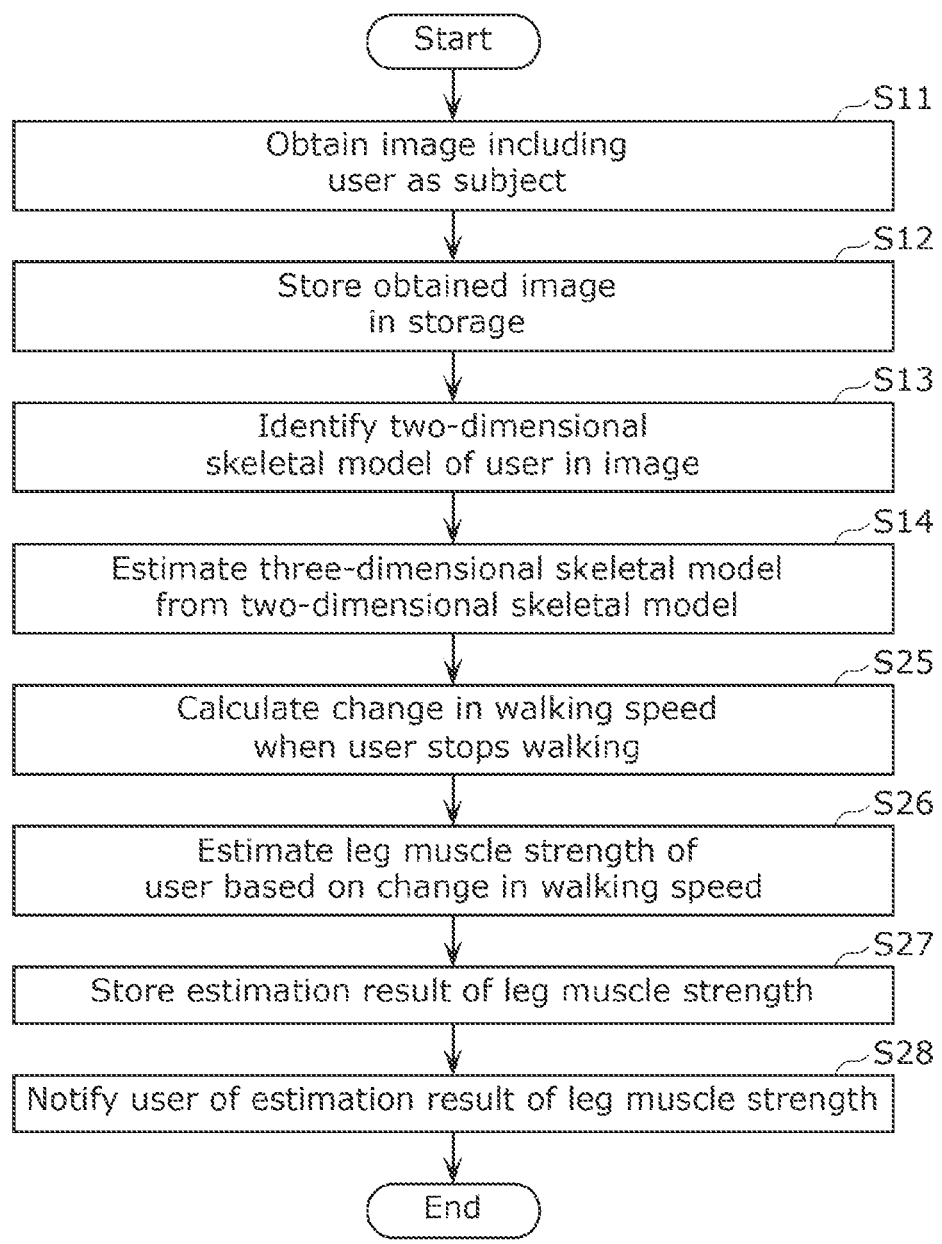
FIG. 9 is a flowchart of operation example 2 of the leg muscle strength estimation system according to the embodiment.

Next, operation example 2 of leg muscle strength estimation system 10 will be given. FIG. 9 is a flowchart of operation example 2 of leg muscle strength estimation system 10.

As steps S11 through S14 are the same as in operation example 1, detailed description thereof will be omitted. After step S14, estimator 35 calculates a change in walking speed (an amount of change in walking speed; i.e., acceleration) of the user when the user stops walking (S25).

First, estimator 35 identifies, in a video, which is a collection of images (hereinafter also referred to as frames) stored in storage 33, a frame in which movement of the three-dimensional skeletal model (displacement of the coordinates of the joints) has fallen below a predetermined value. In other words, estimator 35 identifies a frame believed to capture the user who has come to a stop after walking.

Next, estimator 35 calculates a change in walking speed of the user when the user stops walking, based on a frame captured within a predetermined period that ends at the frame identified in step S25. For example, estimator 35 can calculate the change in walking speed based on the displacement of the coordinates of the joints in the direction of travel.

Next, estimator 35 estimates the leg muscle strength of the user based on the calculated change in walking speed (S26). According to the inventors' knowledge, it can be concluded that the faster the user can come to a stop while walking (stated differently, the greater the change in walking speed), the greater the leg muscle strength of the user is. Therefore, the greater the change in walking speed of the user when the user stops walking is, the greater estimator 35 estimates the leg muscle strength of the user to be.

Estimator 35 stores the estimation result of the leg muscle strength in storage 33 (S27). For example, estimator 35 converts the magnitude of the change in walking speed into a muscle strength value and stores this value in storage 33 by using reference data that is stored in advance in storage 33 and indicates associations between magnitudes of change in walking speed and muscle strength values.

Estimator 35 then notifies the user of the estimation result of the leg muscle strength when necessary (S28). For example, estimator 35 estimates the leg muscle strength and stores the estimation result at fixed intervals, and when, for example, the data indicates a downward (or upward) trend in leg muscle strength, causes communicator 34 to transmit the notification information. The notification information is received by display apparatus 40 via server apparatus 50, and as a result, a notification screen for the leg muscle strength, like that in FIG. 8, is displayed on display 41.

As described above, in operation example 2, obtainer 31 obtains a video comprising a plurality of images, and estimator 35 estimates the leg muscle strength of the user based on a change in walking speed of the user when the user stops walking, which is identified using the obtained video. This makes it possible to easily obtain leg muscle strength data as a result of the user simply walking as usual within the image capturing range of camera 20.

Variation Example of Three-dimensional Skeletal Model Estimation Method

Note that in operation example 1 and operation example 2 described above, leg muscle strength is estimated based on an image captured by a single camera 20 disposed in a predetermined position, but leg muscle strength may be estimated based on images captured by a plurality of cameras 20. In such cases, leg muscle strength estimation system 10 can estimate the three-dimensional skeletal model without using a learning model.

Moreover, in operation example 1 and operation example 2 described above, the three-dimensional skeletal model may be estimated using, as camera 20, a 3D camera that includes a function of emitting infrared light in the image capturing range. However since the functionality of such a 3D camera decreases outdoors, use of a normal camera 20 in outdoor applications is effective.

When camera 20 is provided in a position that allows for the user to be captured from the side (i.e., when camera 20 can capture an image from which the knee flexion angle is directly identifiable, such as the image in FIG. 6 or FIG. 7), there is no need to estimate a three-dimensional skeletal model.

Variation Example of Leg Muscle Strength Evaluation Method

In operation example 1 and operation example 2, the current leg muscle strength of a specific user is evaluated to determine whether it is exhibiting a downward trend or not based on changes in leg muscle strength of a specific user, but the current leg muscle strength of a specific user may be evaluated based on a comparison with an average leg muscle strength of a number of unspecified users.

For example, server apparatus 50 can collect estimation results along with user attribute information (e.g., age, sex, height, weight, etc.) from a plurality of estimation apparatuses 30 and store this as big data. Estimator 35 can reference the big data by accessing server apparatus 50 using communicator 34. Estimator 35 may evaluate the leg muscle strength of a specific user by comparing an estimated muscle strength value of the specific user to the average muscle strength value of a number of unspecified users having the same attribute information as the specific user.

For example, when the leg muscle strength of a specific user is evaluated by comparison with the leg muscle strength of a number of unspecified users having a substantially similar physique to the specific user, user input receiver 42 of display apparatus 40 receives an input of information indicating the physique of the specific user (for example, body height information and body weight information) from the specific user. In such cases, user input receiver 42 functions as a body height information obtainer that obtains body height information on the user.

Note that the two-dimensional skeletal model and the three-dimensional skeletal model described above do not include information related to absolute body size. Accordingly, when a user with a large physique appears small in the image, the user may inadvertently be handled as a user with a small physique. The body height information is therefore useful as information for providing the two-dimensional skeletal model and the three-dimensional skeletal model described above with the absolute body size of the user.

Variation Example for Improving Estimation Accuracy

Figure 10:
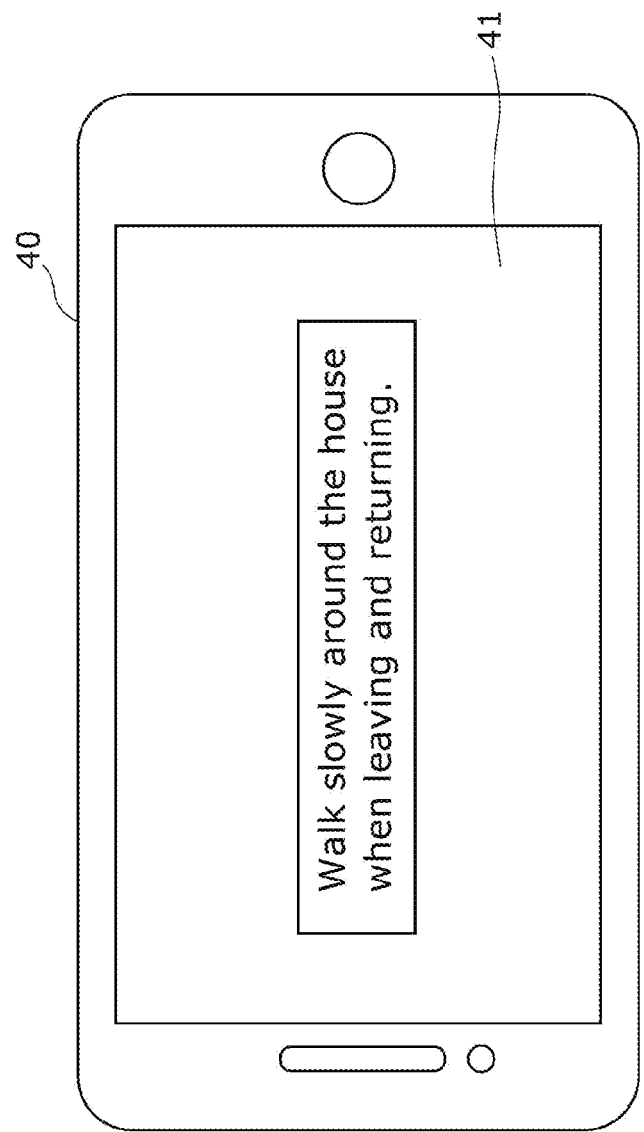
FIG. 10 illustrates one example of an instruction screen that instructs the user how to walk.

Since variations in how the user walks may be a factor that reduces leg muscle strength estimation accuracy, a screen instructing the user how to walk may be displayed on display 41 in display apparatus 40. FIG. 10 illustrates one example of an instruction screen that instructs the user how to walk.

For example, estimator 35 may transmit instruction information that instructs the user how to walk to communicator 34 at fixed intervals. The instruction information is received by display apparatus 40 via server apparatus 50, and as a result, the instruction screen illustrated in FIG. 10 is displayed on display 41. In such cases, display 41 functions as an instructor that instructs the user how to walk. Note that display 41 need not function as the instructor; a speaker (not illustrated in the drawings) included in display apparatus 40 may function as the instructor. In other words, the user may be instructed how to walk via audio.

Although the instruction screen illustrated in FIG. 10 is a screen instructing the user to walk slowly, the instruction screen may be a screen instructing the user to walk quickly. The instruction screen may be a screen instructing a step length or a stride width.

Such an instruction screen can improve leg muscle strength estimation accuracy.

Advantageous Effects, Etc.

As described above, leg muscle strength estimation system 10 includes: obtainer 31 that obtains an image including a user that is walking as a subject of the image; and estimator 35 that estimates a leg muscle strength of the user based on the image obtained.

Leg muscle strength estimation system 10 configured in this way can estimate the leg muscle strength of the user without contacting the user. For example, if camera 20 is disposed on, for example, the exterior wall of a home, leg muscle strength estimation system 10 can estimate the leg muscle strength of the user based on an image captured when the user leaves and returns home as usual, and it is therefore possible to know the state of the user's leg muscle strength without requiring any special action by the user.

Moreover, for example, estimator 35 estimates the leg muscle strength of the user based on a knee flexion angle of the user while the user is walking, the knee flexion angle being identified using the image obtained.

Leg muscle strength estimation system 10 configured in this way can estimate the leg muscle strength of the user based on the knee flexion angle of the user.

Moreover, for example, the smaller the knee flexion angle of the user while the user is walking is, the greater estimator 35 estimates the leg muscle strength of the user to be.

Leg muscle strength estimation system 10 configured in this way can appropriately estimate the leg muscle strength of the user based on the knee flexion angle of the user.

Moreover, for example, obtainer 31 obtains a video comprising a plurality of images each of which is the image, and estimator 35 estimates the leg muscle strength of the user based on a change in walking speed of the user when the user stops walking, the change in walking speed being identified using the video obtained.

Leg muscle strength estimation system 10 configured in this way can estimate the leg muscle strength of the user based on a change in walking speed of the user when the user stops walking.

Moreover, for example, the greater the change in walking speed of the user when the user stops walking is, the greater estimator 35 estimates the leg muscle strength of the user to be.

Leg muscle strength estimation system 10 configured in this way can appropriately estimate the leg muscle strength of the user based on a change in walking speed of the user when the user stops walking.

Moreover, for example, the image is captured by a single camera 20 disposed in a predetermined position, and estimator 35: identifies a two-dimensional skeletal model of the user based on the image obtained; uses a machine learning model to estimate a three-dimensional skeletal model of the user based on the two-dimensional skeletal model identified; and estimates the leg muscle strength of the user based on the three-dimensional skeletal model estimated.

Leg muscle strength estimation system 10 configured in this way can estimate the leg muscle strength of the user based on an image obtained from a single camera 20.

Moreover, for example, the single camera 20 is disposed in the predetermined position outdoors.

Leg muscle strength estimation system 10 configured in this way can estimate the leg muscle strength of the user based on an image obtained from a single, normal camera 20 disposed outdoors.

Moreover, for example, leg muscle strength estimation system 10 further includes: user input receiver 42 that obtains body height information on the user. Estimator 35 uses the body height information obtained to evaluate the leg muscle strength of the user estimated. User input receiver 42 is one example of the body height information obtainer.

Leg muscle strength estimation system 10 configured in this way can evaluate the estimated leg muscle strength of the user based on the body height information on the user.

Moreover, for example, leg muscle strength estimation system 10 further includes display 41 that instructs the user how to walk.

Leg muscle strength estimation system 10 configured in this way can improve leg muscle strength estimation accuracy.

Moreover, for example, obtainer 31 is a communication circuit that obtains the image captured by camera 20, estimator 35 is a computer, and the computer estimates the leg muscle strength of the user based on the image captured by camera 20 and displays a result of the estimation on display apparatus 40 connected to the computer, or display apparatus 40 of a terminal connected to the computer over a network.

Leg muscle strength estimation system 10 configured in this way can provide the user with the result of the leg muscle strength estimation.

Moreover, for example, the computer displays an instruction on how to walk on display apparatus 40 connected to the computer or display apparatus 40 of the terminal, the instruction being in accordance with the result of the estimation of the leg muscle strength.

Leg muscle strength estimation system 10 configured in this way can instruct the user how to walk.

A leg muscle strength estimation method executed by a computer such as leg muscle strength estimation system 10 includes: obtaining an image including a user that is walking as a subject of the image; and estimating a leg muscle strength of the user based on the image obtained.

Such a leg muscle strength estimation method can estimate the leg muscle strength of the user without contacting the user. For example, if camera 20 is disposed on, for example, the exterior wall of a home, the leg muscle strength estimation method can estimate the leg muscle strength of the user based on an image captured when the user leaves and returns home as usual, and it is therefore possible to know the state of the user's leg muscle strength without requiring any special action by the user.

Other Embodiments

Although the above describes the leg muscle strength estimation system and the leg muscle strength estimation method according to an embodiment, the present invention is not limited to the above embodiment.

For example, in the above embodiment, the camera is described as being disposed outdoors, but the camera may be disposed indoors. Moreover, the camera may be disposed in a building other than a home, such as a nursing home or a public institution, and may be disposed on a utility pole or the like.

Moreover, in the above embodiment, the image captured by the camera includes, as the subject of the image, the user walking as they go about their day routinely, but the image may include, as the subject of the image, the user walking deliberately for the purpose of measuring leg muscle strength.

Moreover, in the above embodiment, the leg muscle strength estimation system is implemented via a plurality of apparatuses, but the leg muscle strength estimation system may be implemented as a single apparatus. When the leg muscle strength estimation system is implemented via a plurality of apparatuses, the elements included in the leg muscle strength estimation system may be distributed among the plurality of apparatus in any manner so long as the leg muscle strength estimation system is capable of estimating the user's leg muscle strength. For example, the obtainer and the estimator according to the above embodiment may be included in the server apparatus rather than in the estimation apparatus.

Moreover, in the above embodiment, each element may be realized as dedicated hardware, or may be realized by executing a software program suitable for the element. Each element may be realized by a program executing unit, such as a CPU or a processor, reading and executing the software program recorded on storage such as a hard disk or semiconductor memory.

Moreover, each element may be a circuit (or integrated circuit). These circuits may be consolidated as a single circuit and, alternatively, may be individual circuits. Moreover, these circuits may be ordinary circuits and, alternatively, may be specialized circuits.

General or specific aspects of the present disclosure may be realized as a system, device, method, integrated circuit, computer program, or computer-readable recording medium, such as a CD-ROM, or any combination thereof. For example, the present invention may be realized as a program for causing a computer to execute the leg muscle strength estimation method according to the above embodiment, and, alternatively, may be realized as a non-transitory computer-readable recording medium on which such a program is recorded.

The orders of the processes in the flow charts of the operation examples described in the above embodiment are non-limiting examples. The processing order may be rearranged, and, alternatively, the processes may be performed in parallel. A process executed by a certain processing unit may be executed by a different processing unit.

Additionally, embodiments arrived at by those skilled in the art making modifications to the above embodiment, as well as embodiments arrived at by combining various elements and functions described in the above embodiment without materially departing from the novel teachings and advantages of the present invention are intended to be included within the scope of the present invention.

REFERENCE SIGNS LIST 10 leg muscle strength estimation system
20 camera
31 obtainer
35 estimator
40 display apparatus
41 display (instructor)
42 user input receiver (body height information obtainer)

The invention claimed is:

1. A leg muscle strength estimation system, comprising:
a camera that obtains an image including a user that is walking as a subject of the image; and
a processor and a memory storing a program, wherein:
the program, when executed by the processor, causes the processor to:
identify a two-dimensional skeletal model of the user based on the image obtained;
use a machine learning model to estimate a three-dimensional skeletal model of the user based on the two-dimensional skeletal model identified;
obtain a knee flexion angle of the user while the user is walking based on the three-dimensional skeletal model estimated; and
estimate a leg muscle strength of the user based on the knee flexion angle of the user, and
the smaller the knee flexion angle of the user while the user is walking is, the greater the leg muscle strength of the user is estimated to be.

2. A leg muscle strength estimation system, comprising:
a camera that obtains a video comprising a plurality of images including a user that is walking as a subject; and
a processor and a memory storing a program, wherein:
the program, when executed by the processor, causes the processor to:
identify a two-dimensional skeletal model of the user based on the plurality of images;
use a machine learning model to estimate a three-dimensional skeletal model of the user based on the two-dimensional skeletal model;
identify a timing that the user stops walking based on the three-dimensional skeletal model estimated; and
estimate the leg muscle strength of the user based on a change in walking speed of the user when the user stops walking,
wherein the greater the change in walking speed of the user when the user stops walking is, the greater the leg muscle strength of the user is estimated to be.

3. The leg muscle strength estimation system according to claim 1, wherein the camera is a single camera disposed in a predetermined position.

4. The leg muscle strength estimation system according to claim 3, wherein the single camera is disposed in the predetermined position outdoors.

5. The leg muscle strength estimation system according to claim 1, wherein:
the executed program further causes the processor to obtain body height information on the user, and use the body height information obtained to evaluate the leg muscle strength of the user estimated.

6. The leg muscle strength estimation system according to claim 1, wherein the executed program furhter causes the processor to instruct the user how to walk.

7. The leg muscle strength estimation system according to claim 1, further comprising:
a communication circuit that obtains the image captured by the camera;
wherein the executed program causes the processor to display a result of the estimation on a display apparatus connected to the processor, or a display apparatus of a terminal connected to the processor over a network.

8. The leg muscle strength estimation system according to claim 7, wherein the executed program causes the processor to display an instruction on how to walk on the display apparatus connected to the processor or the display apparatus of the terminal, the instruction being in accordance with the result of the estimation of the leg muscle strength.

9. A leg muscle strength estimation method executed by a computer, the leg muscle strength estimation method comprising:
obtaining an image, by using a camera, including a user that is walking as a subject of the image;
identifying, by the computer, a two-dimensional skeletal model of the user based on the image obtained;
using, by the computer, a machine learning model to estimate a three-dimensional skeletal model of the user based on the two-dimensional skeletal model identified;
obtaining, by the computer, a knee flexion angle of the user while the user is walking based on the three-dimensional skeletal model estimated; and
estimating, by the computer, a leg muscle strength of the user based on a knee flexion angle of the user while the user is walking, the knee flexion angle being identified using the image obtained,
wherein the smaller the knee flexion angle of the user while the user is walking is, the greater the leg muscle strength of the user is estimated to be.

10. A non-transitory computer-readable recording medium having recorded thereon a program for causing the computer to execute the leg muscle strength estimation method according to claim 9.

* * * * *